(12) United States Patent
O'Reilly

(10) Patent No.: US 6,488,923 B2
(45) Date of Patent: Dec. 3, 2002

(54) **USE OF A FLAVONOID EXTRACT OF *GINKGO BILOBA* SUBSTANTIALLY DEVOID OF TERPENES, IN THE DENTIBUCCAL FIELD, AND COMPOSITION CONTAINING SUCH EXTRACT**

(75) Inventor: Joseph O'Reilly, Glounthaune (IE)

(73) Assignee: Societe de Conseils de Recherches et d'applications Scientifiques (FR)

(*) Notice: Subject to any disclaimer, the term of this patent is extended or adjusted under 35 U.S.C. 154(b) by 0 days.

(21) Appl. No.: 09/994,351

(22) Filed: Nov. 26, 2001

(65) Prior Publication Data

US 2002/0064571 A1 May 30, 2002

Related U.S. Application Data

(62) Division of application No. 09/603,447, filed on Jun. 23, 2000, now Pat. No. 6,340,345, which is a division of application No. 09/284,125, filed as application No. PCT/FR97/01910 on Oct. 24, 1997, now Pat. No. 6,159,450.

(30) Foreign Application Priority Data

Oct. 25, 1996 (FR) ............................................ 96 13065

(51) Int. Cl.$^7$ .......................... A01N 65/00; A61K 35/78
(52) U.S. Cl. ............................... 424/78.03; 424/78.02; 424/78.05; 424/752
(58) Field of Search .......................... 424/78.02, 78.03, 424/78.05, 752

(56) References Cited

U.S. PATENT DOCUMENTS 5,145,781 A * 9/1992 Suzuki et al. .................. 435/99
5,578,307 A * 11/1996 Wunderlich et al. ......... 424/451
5,686,082 A * 11/1997 N'Guyen .................... 424/450
5,780,060 A * 7/1998 Levy et al. ................. 424/451

* cited by examiner

*Primary Examiner*—Herbert J. Lilling
(74) *Attorney, Agent, or Firm*—Bierman, Muserlian and Lucas

(57) ABSTRACT

Cosmetic compositions containing the flavonoid extract of *Ginkgo biloba* leaves substantially free of terpenes and a cosmetic carrier.

7 Claims, No Drawings

USE OF A FLAVONOID EXTRACT OF GINKGO BILOBA SUBSTANTIALLY DEVOID OF TERPENES, IN THE DENTIBUCCAL FIELD, AND COMPOSITION CONTAINING SUCH EXTRACT

This application is a division of U.S. patent application Ser. No. 09/603,447 filed Jun. 23, 2000, now U.S. Pat. No. 6,340,345 which is a division of U.S. patent application Ser. No. 09/284,125 filed Apr. 6, 1999, now U.S. Pat. No. 6,159,450 which is a 371 of PCT/FR97/01910 filed Oct. 24, 1997.

The invention relates to the use of a flavonoid extract of *Ginkgo biloba*, and more specifically an extract substantially devoid of terpenes, in the dentibuccal field. The invention also relates to an dentibuccal composition containing such extract.

A flavonoid extract of *Ginkgo biloba* leaves devoid of terpenes according to the invention comprises flavonoid glycosides and little or no terpenes. When the extract contains terpenes, the terpene content is 1% maximum, and preferably 0.5% maximum. This extract contains from 28 to 35% of flavonoid glycosides, and preferably 28 to 32%. Such extracts are preferably obtained from leaves from pruned young ginkgo biloba trees.

A subject of the invention is a process for obtaining such an extract, a process which comprises several extraction stages of *Ginkgo biloba* leaves by solvents and characterized in that one of the extraction stages is a deterpenation stage and the solvent used is a compound of formula RC(O)OR' in which R and R' represent, independently, a lower alkyl, alone or mixed with a saturated aliphatic hydrocarbon containing at least 5 carbon atoms. The extraction stage can be carried out at any stage in the process. Preferably, the solvent used during the deterpenation stage contains from 0 to 20% of saturated aliphatic hydrocarbon.

Extraction stages other than the deterpenation stage are known in the literature in particular in Patents EP431535, EP 431536, EP 360556 and EP324197. These Patents are incorporated into the present Application by way of reference.

In the definitions indicated above, the expression lower alkyl preferably represents a linear or branched alkyl radical having from 1 to 6 carbon atoms, and in particular an alkyl radical having from 1 to 4 carbon atoms such as the methyl, ethyl, propyl, isopropyl, butyl, isobutyl, sec-butyl and tert-butyl radicals. The solvents of formula RC(O)OR' in which the radicals R and R' represent methyl, ethyl or propyl and in particular ethyl acetate are preferably used. The saturated aliphatic hydrocarbon can be chosen from hexane, heptane and octane. Preferably, heptane is used.

A flavonoid extract of *Ginkgo biloba* leaves as defined above has an anti-elastasic and anti-inflammatory activity on human gums. An illustration of these properties is to be found below in the experimental part.

These properties render the Ginkgo extract as defined above suitable for pharmaceutical use. A subject of the present Application is therefore, as a medicament, and in particular as a medicament intended for the dentibuccal sphere, a flavonoid extract of *Ginkgo biloba* leaves as defined above.

A subject of the invention is also a pharmaceutical composition intended in particular for the treatment of the dentibuccal sphere and containing as active ingredient a flavonoid extract of *Ginkgo biloba* leaves as defined above, optionally combined with a pharmaceutically acceptable support.

A more particular subject of the invention is an anti-elastasic pharmaceutical composition containing, as an anti-elastasic agent, at least one effective quantity of a Ginkgo extract as defined above. A more particular subject of the invention is also an anti-inflammatory pharmaceutical composition containing, as an anti-inflammatory agent, at least one effective quantity of a Ginkgo extract as defined above.

A pharmaceutical composition according to the invention preferably contains from 0.05 to 0.6% of Ginkgo extract, and preferentially from 0.1 to 0.5%. Such a composition can also contain at least one other agent having similar or complementary activities. Preferably, a pharmaceutical composition according to the invention contains ginkgo extract as defined above combined with ceramides. Preferentially, such a composition contains from 0.1 to 0.5% of Ginkgo extract and from 0.05 to 0.3% of ceramides.

A pharmaceutical composition according to the invention can be presented in any appropriate form according to the chosen administration method. It can be presented in liquid form such as, for example, a solution, a suspension or an emulsion. It can also be presented in the form of a gel, spray, toothpaste or chewing gum. It is preferably presented in the form of a gel or chewing gum. It can contain, in addition to the ginkgo extract, alone or in combination, and an appropriate support, the ingredients or adjuvants commonly used for producing such compositions.

A subject of the invention is also the use of a flavonoid extract of Ginkgo as defined above for the preparation of a pharmaceutical composition intended for treatment in the dentibuccal sphere.

A more particular subject of the invention is the use of a flavonoid extract of Ginkgo as defined above for the preparation of a pharmaceutical composition intended to inhibit elastase. A more particular subject of the invention is also the use of a flavonoid extract of Ginkgo as defined above for the preparation of pharmaceutical composition intended to inhibit inflammation in the dentibuccal sphere. Such a flavonoid extract can be used alone or in combination with another agent having similar or complementary properties according to the sought result, optionally in the presence of an appropriate support. An extract as defined above is preferably used in combination with ceramides.

Ceramides are sphingolipids present in all cell structures. They are also notably present in the plant world and in particular in wheat, rice, soya, millet and spinach. They can also be synthsized. Owing to their structure, they can advantageously be used as a vector, considerably increasing the bioavailability of the active agent they are conveying. The term ceramide used in the present Application has the standard meaning known to a person skilled in the art. The term ceramide thus includes all ceramides, of synthetic or natural origin (vegetable, animal or human) optionally substituted, for example, by a sugar such as mono- or polyglucosylceramides.

Owing to a high flavonoid glycoside content, the state of the art suggests that an extract as defined above has an anti-oxidant and anti-radicular activity. Moreover, given on the one hand its anti-inflammatory, anti-elastasic properties but also vasoregulatory and collagen activating properties and, on the other hand, an almost total absence of terpenes in its composition, such an extract can advantageously be used in cosmetics or in dermatology.

A subject of the invention is also the use of a flavonoid extract of *Ginkgo biloba* leaves as defined above for the preparation of a vasoregulatory and/or collagen activating medicament. The invention also relates to the use of a cosmetic composition containing a flavonoid extract as defined above as a vasoregulator and/or a collagen activator. A subject of the invention is also a cosmetic treatment method characterized in that a flavonoid extract is used as defined above as a vasoregulator and/or a collagen activator.

A subject of the invention is also a cosmetic composition intended in particular for the dentibuccal sphere and containing a flavonoid extract of *Ginkgo biloba* leaves as defined above. This extract can be used on its own or in combination with at least one other agent having a similar or complementary activity, and optionally with an appropriate support. Preferably, the Ginkgo extract is used in combination with ceramides. A cosmetic composition according to the invention can contain from 0.05 to 0.6% of Ginkgo extract as defined above, and from 0.05 to 0.3% of ceramides. Such a composition can be presented in any appropriate form for this type of use such as creams, emulsions, milks, gels, oils, makeup products, lipsticks and lotions. In addition to Ginkgo extract, alone or in combination, and an appropriate support, it can contain the ingredients or adjuvants commonly used to produce such compositions.

A subject of the invention is also a flavonoid extract of *Ginkgo biloba* as defined above for the cosmetic treatment of affections in the dentibuccal sphere and in particular gingivitis.

The following examples are presented in order to illustrate the invention and should in no event be considered to limit the scope of the invention.

Experimental Part

Process for obtaining a flavonoid extract

Ginkgo biloba leaves are extracted with from 6 to 12 parts (preferably 8 parts) of water containing 60% acetone at 50–60° C. and the solution is concentrated in order to reduce the percentage of acetone to less than 3%. This solution is cooled down and the lipids are eliminated by decanting. The aqueous solution is extracted with 2 to 5 parts of ethyl acetate containing from 0 to 20% heptane. The resultant solution is extracted with a minimum quantity of an acetone/butanol mixture (percentage acetone 0 to 15%) in the presence of ammonium sulphate. The organic phase is concentrated; after ethanol has been added, the solution is again concentrated. After further dilution with ethanol, the solutions is cooled down and the insoluble precipitates are filtered out. The resultant solution is concentrated, dried and finely ground in order to recover the flavonoid extract in the form of a homogenous powder.

Study of the anti-elastasic and anti-inflammatory activity of a flavonoid extract of *Ginkgo biloba* substantially devoid of terpene 1—Study of anti-elastasic activity ex vivo The purpose of this study is therefore to study the anti-elastasic activity of an extract as defined above, alone or in combination with ceramides. This activity is evaluated on sections of human gums.

The ceramides used, of vegetable origin, are obtained according to a process as described in Patent FR 2676936 incorporated by way of reference, a process which comprises exctraction from wheat, using a polar extraction solvent followed by recrystallization from an organic solvent. They are essentially composed of glucosylceramides and ceramides.

For this purpose, the elastic fibre network is subjected to human leucocyte elastase (HLE), with or without an anti-elastasic product. The elastic fibres remaining after enzymatic action are stained with (+)catechin.

Frozen sections of 8 μm are carried out from 5 samples obtained from biopsies of normal buccal mucosa, taken during dental extractions.

Protocol:

In a first stage, the concentration in human leucocyte elastase required for the destruction of elastic fibres is determined: leucocyte elastase is applied to the skin sections for two hours at ambient temperature and in a humid atmosphere; after fixing in acetone and dehydration in ethanol at 70° C., the remaining elastic fibres are stained with (+)catechin. Total destruction of the elastic fibres is obtained in the presence of 10 μm/ml of human leucocyte elastase.

In order to demonstrate any fixing of the products on the enzyme, similar quantities of products, in the form of an emulsion, and of human leucocyte elastase at 10 μm/ml are applied simultaneously to the sections for two hours, at ambient temperature. The anti-elastic activity of the products is compared with that of (PMSF), a powerful elastase inhibitor.

Morphometric quantification—by image analysis—produces the results which are shown in Table 1 below.

TABLE 1

% of elastic fibres remaining after treatment with human leucocyte elastase in the presence of a ginkgo extract alone or in combination with ceramides

|  |  |  | upper corium dermis | medium corium dermis | lower corium dermis |
| --- | --- | --- | --- | --- | --- |
| HLE alone |  |  | 0 | 0 | 0 |
| HLE + PMSF |  |  | 25 | 55 | 70 |
| Ginkgo extract (in %) | + | Ceramide (in %) |  |  |  |
| 0 |  | 0.1 | 0 | 0 | 27.65 |
| 0 |  | 0.2 | 0 | 0 | 22.50 |
| 0.1 |  | 0 | 0 | 0 | 13.85 |
| 0.3 |  | 0 | 0 | 0 | 33 |
| 0.5 |  | 0 | 2.5 | 31.85 | 61.20 |
| 0.1 |  | 0.1 | 0 | 0 | 24.5 |
| 0.3 |  | 0.1 | 0 | 17.6 | 23 |
| 0.5 |  | 0.1 | 56.7 | 47 | 65 |
| 0.1 |  | 0.2 | 0 | 0 | 15.2 |
| 0.3 |  | 0.2 | 0 | 19 | 30 |
| 0.5 |  | 0.2 | 70 | 53.2 | 80 |

2—Study of anti-inflammatory activity

The composition tested in this study is presented in the form of a gel and comprises 0.5% of Ginkgo extract as defined above and 0.1% of vegetable ceramide as defined in the anti-elastasic activity study.

The study is carried out on 20 patients suffering from mild and moderate tartaric gingivitis. The patients apply the gel twice daily for one month, at the level of their gingival mucosa. Clinical assessment of their gingival state is carried out on days $D_0$ and $D_{28}$ using a scoring system. The main evaluation criteria are an assessment of erythema and gingivitis. The anti-inflammatory action of the treatment must be demonstrated by a reduction in erythema and a reduction in gingivitis.

Clinically, erythema is demonstrated by an erythematous appearance (red colour) of the gum and a high grade of gingivitis. The gum's return to a normal state, a reduction in the erythema, the gingivitis stage and the extent of the condition constitute clinical proof of anti-inflammatory activity.

Secondary criteria are an assessment of spontaneous pain and pain on chewing, and of bleeding (intensity and topography).

Operation of criteria:

The three main criteria indicating the extent of the inflammatory activity, "gingivitis", "colour of gum" and "topography of condition" are assigned a coefficient of 2 with respect to the results expressed.

The "spontaneous pain", "pain on chewing" and "papillary bleeding" (intensity and topography) are assigned a coefficient of 1 with respect to the results expressed.

For the evaluation of the gingivitis, the scores are as follows:
- (0) if the grade is 0: gum normal, no inflammation, no change in colour, no bleeding;
- (2) if the grade is 1: slight gingivitis, slight inflammation, slight alteration in the gingival surface, no bleeding;
- (4) if the grade is 2: moderately extended gingivitis, moderate inflammation, erythema, oedema, bleeding on probing or applying pressure;
- (6) if the grade is 3: very extensive gingivitis, severe inflammation, pronounced erythema, oedema, tendency towards spontaneous bleeding, ulceration.

For the evaluation of the colour of the gum, the scores are as follows:
- (0) normal
- (2) slight erythema
- (4) moderate erythema
- (6) severe erythema Topographical evaluation of the colour of the gum:

Six sectors are defined: RiUp, FrUp, LeUp, RiLo, FrLo and LeLo (Fr, Up, Lo, Ri and Le respectively signify Front, Upper, Lower, Right and Left).
- (0) no sectors affected
- (2) one sector affected
- (4) two sectors affected
- (6) three sectors affected
- (8) more than three sectors affected For the evaluation of papillary bleeding (Engelberger et Coll., 1993), the scores are as follows:
- (0) if the grade is 0: no bleeding 10 to 30 seconds after probing
- (2) if the grade is 1: slight bleeding (fine trickle of blood)
- (4) if the grade is 2: moderate bleeding
- (6) if the grade is 3: intense bleeding Topographical evaluation of papillary bleeding:
- (0) no sectors affected
- (1) one sector affected
- (2) two sectors affected
- (3) three sectors affected
- (4) more than three sectors affected Changes in the "spontaneous pain and pain on chewing" criteria are evaluated using a visual scale on $D_0$ and $D_{28}$:
- (0) if no pain or slight pain (measurement between 0 and 2.5 cm on the visual scale)
- (1) if moderate pain (measurement between 2.5 and 5 cm on the visual scale)
- (2) if significant pain (measurement between 5 and 7.5 cm on the visual scale)
- (3) if severe pain (measurement between 7.5 and 10 cm on the visual scale)

An overall score is then calculated by adding together the individual scores.

a return to a normal state corresponds to a score of 0.

maximum gravity corresponds to a score of 33.

The results are set out in Table 2 below.

TABLE 2

|  | Day $D_0$ | Day $D_{28}$ |
|---|---|---|
| Evaluation of gingivitis | 3.50 ± 1 | 1.0 ± 1.2 (p < 0.05) |
| Evaluation of the colour of the gum (erythema) | 4.00 ± 1.4 | 1.1 ± 1.45 (p < 0.05) |
| Topography of gingival erythema | 4.80 ± 1.7 | 1.6 ± 11.8 (p < 0.05) |
| Evaluation of papillary bleeding | 0.85 ± 0.8 | 0.1 ± 0.43 (p < 0.05) |
| Topography of papillary bleeding | 1.20 ± 1.12 | 0.1 ± 0.43 (p < 0.05) |
| Evaluation of spontaneous pain | 1.35 ± 1.2 | 0 (p < 0.05) |
| Evaluation of pain on chewing | 1.10 ± 1.17 | 0 (p < 0.05) |
| Overall score | 16.80 ± 4.8 | 3.9 ± 4.6 (p < 0.05) |

This study on 20 patients suffering from tartaric gingivitis demonstrated the anti-inflammatory activity of a Ginkgo extract as defined previously in combination with vegetable ceramides.

This anti-inflammatory activity takes the significant clinical form of a disappearance of gingivitis and gingival erythema in 11 cases out of 20 and an improvement in 8 other cases.

A signficant improvement in the score for papillary bleeding and a complete disappearance, in all cases, of gingival pain (spontaneous and on chewing) were observed.

What is claimed is:

1. A cosmetic composition containing a flavonoid extract of *Ginkgo biloba* leaves comprising 28 to 35% by weight of flavonoid glycosides and substantially free of terpenes, said extraction being several stages of extraction with solvents with one extraction being a deterpenation extract with a compound of the formula

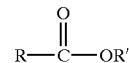

wherein R and R' are independently lower alkyl optionally admixed with a saturated aliphatic hydrocarbon of at least 5 carbon atoms.

2. A composition of claim 1 containing 28 to 32% by weight of flavonoid glycosides.

3. A composition of claim 1 wherein the extract contains a maximum of 1% by weight of terpenes.

4. A composition of claim 1 wherein the extract contains a maximum of 0.5% by weight of terpenes.

5. A composition of claim 1 containing 0.05 to 0.6% by weight of said extract.

6. A composition of claim 1 wherein said extract is combined with ceramides.

7. A composition of claim 6 containing 0.05 to 0.3% by weight of ceramides.

* * * * *